(12) United States Patent
Hansen

(10) Patent No.: US 9,795,491 B2
(45) Date of Patent: Oct. 24, 2017

(54) INTERVERTEBRAL DISC PROSTHESIS AND INTERVERTEBRAL PROSTHETIC UNIT

(75) Inventor: Stéphane Hansen, Dijon (FR)

(73) Assignee: Valérie Lemaire, Saulon la Chapelle (FR)

( * ) Notice: Subject to any disclaimer, the term of this patent is extended or adjusted under 35 U.S.C. 154(b) by 880 days.

(21) Appl. No.: 14/111,878

(22) PCT Filed: Apr. 13, 2012

(86) PCT No.: PCT/FR2012/050827
§ 371 (c)(1),
(2), (4) Date: Dec. 4, 2013

(87) PCT Pub. No.: WO2012/140387
PCT Pub. Date: Oct. 18, 2012

(65) Prior Publication Data
US 2014/0107784 A1    Apr. 17, 2014

(30) Foreign Application Priority Data

Apr. 15, 2011   (FR) .................................... 11 01194

(51) Int. Cl.
*A61F 2/44* (2006.01)
*A61B 17/70* (2006.01)
*A61F 2/30* (2006.01)

(52) U.S. Cl.
CPC ........ *A61F 2/4425* (2013.01); *A61B 17/7025* (2013.01); *A61F 2/4405* (2013.01);
(Continued)

(58) Field of Classification Search
CPC .......... A61F 2/44; A61F 2/442; A61F 2/4425; A61F 2002/443; A61F 2002/444;
(Continued)

(56) References Cited

U.S. PATENT DOCUMENTS

| 5,401,269 A * | 3/1995 | Buttner-Janz ......... A61F 2/4425 606/247 |
| 7,338,527 B2 * | 3/2008 | Blatt .................. A61B 17/1757 606/247 |
| 2005/0165487 A1 * | 7/2005 | Muhanna ............... A61F 2/4425 623/17.15 |
| 2006/0036325 A1 * | 2/2006 | Paul ................... A61B 17/1757 623/17.14 |

(Continued)

FOREIGN PATENT DOCUMENTS

| EP | 2140840 | 1/2010 |
| WO | 02089701 A2 | 11/2002 |

(Continued)

OTHER PUBLICATIONS

International Search Report dated Nov. 15, 2012, as issued in corresponding International Patent Application No. PCT/FR2012/050827, filed Apr. 13, 2012.

*Primary Examiner* — Kevin T Truong
*Assistant Examiner* — Tracy Kamikawa
(74) *Attorney, Agent, or Firm* — Maier & Maier, PLLC

(57) ABSTRACT

An intervertebral disc prosthesis (1) having at least one upper plateau (4, 4') and at least one lower plateau (5, 5'), which are separated by two movable cores (6, 6') whose lower face (62, 62') and upper face (61, 61') respectively match a concave surface (54, 54') of the upper plateau (4, 4') and a convex surface (44, 44') of the lower plateau (5, 5'). An intervertebral prosthetic unit (10) is also described having an intervertebral disc prosthesis and a posterior articular prosthesis (11) provided with two adjacent and partially tangent articular blades (12, 13), which are each coupled to a vertebra (3, 3') by coupling devices (14) and are connected by guide devices that allow them to move along a curve whose center C3 is provided on the same side as the implantation of said coupling means.

10 Claims, 3 Drawing Sheets

(52) U.S. Cl.
CPC ... *A61F 2002/304* (2013.01); *A61F 2002/308* (2013.01); *A61F 2002/3065* (2013.01); *A61F 2002/30245* (2013.01); *A61F 2002/30393* (2013.01); *A61F 2002/30616* (2013.01); *A61F 2002/30642* (2013.01); *A61F 2002/443* (2013.01); *A61F 2002/448* (2013.01); *A61F 2310/00023* (2013.01); *A61F 2310/00029* (2013.01); *A61F 2310/00179* (2013.01); *A61F 2310/00796* (2013.01)

(58) Field of Classification Search
CPC ........ A61F 2002/448; A61F 2002/4485; A61F 2002/449
See application file for complete search history.

(56) References Cited

U.S. PATENT DOCUMENTS

| | | | |
|---|---|---|---|
| 2006/0089717 A1* | 4/2006 | Krishna | A61B 17/7025 623/17.11 |
| 2006/0149229 A1* | 7/2006 | Kwak | A61B 17/7023 606/256 |
| 2007/0191952 A1 | 8/2007 | Bernero | |
| 2007/0270958 A1 | 11/2007 | Albans et al. | |
| 2009/0192618 A1* | 7/2009 | Zielinski | A61F 2/4425 623/17.16 |

FOREIGN PATENT DOCUMENTS

| | | | |
|---|---|---|---|
| WO | 2006105603 A1 | 10/2006 | |
| WO | 2010015755 A2 | 2/2010 | |

* cited by examiner

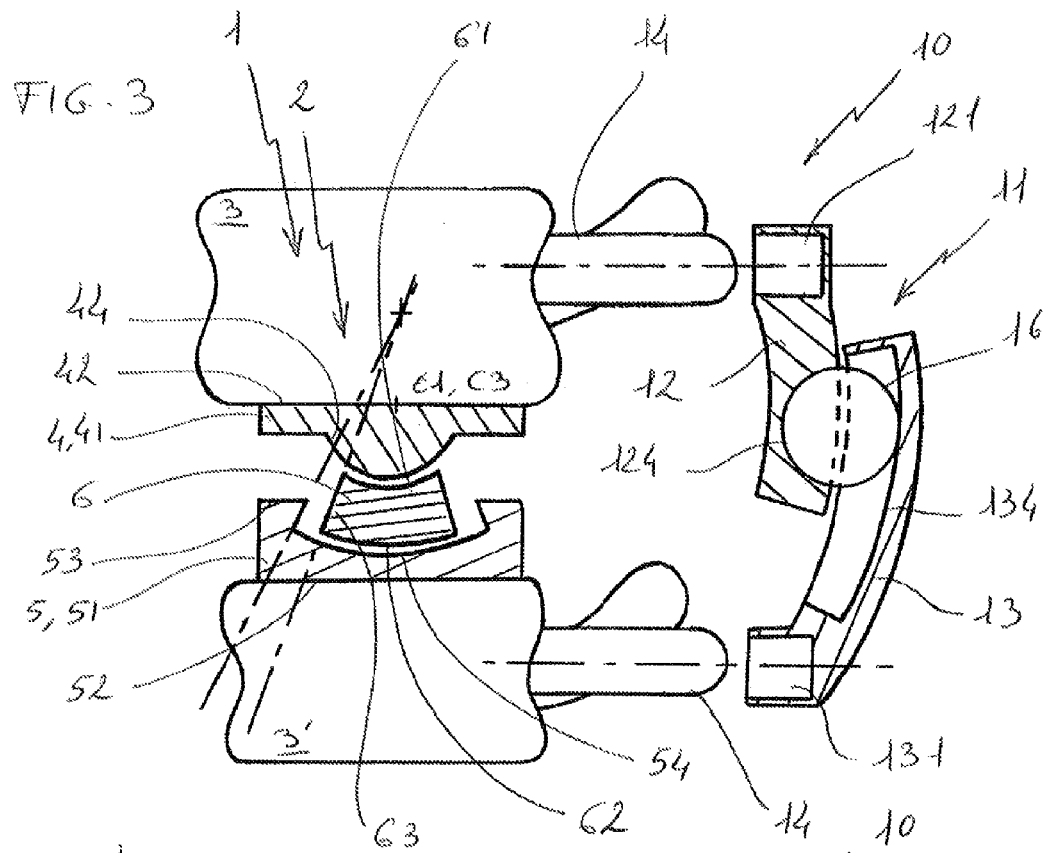
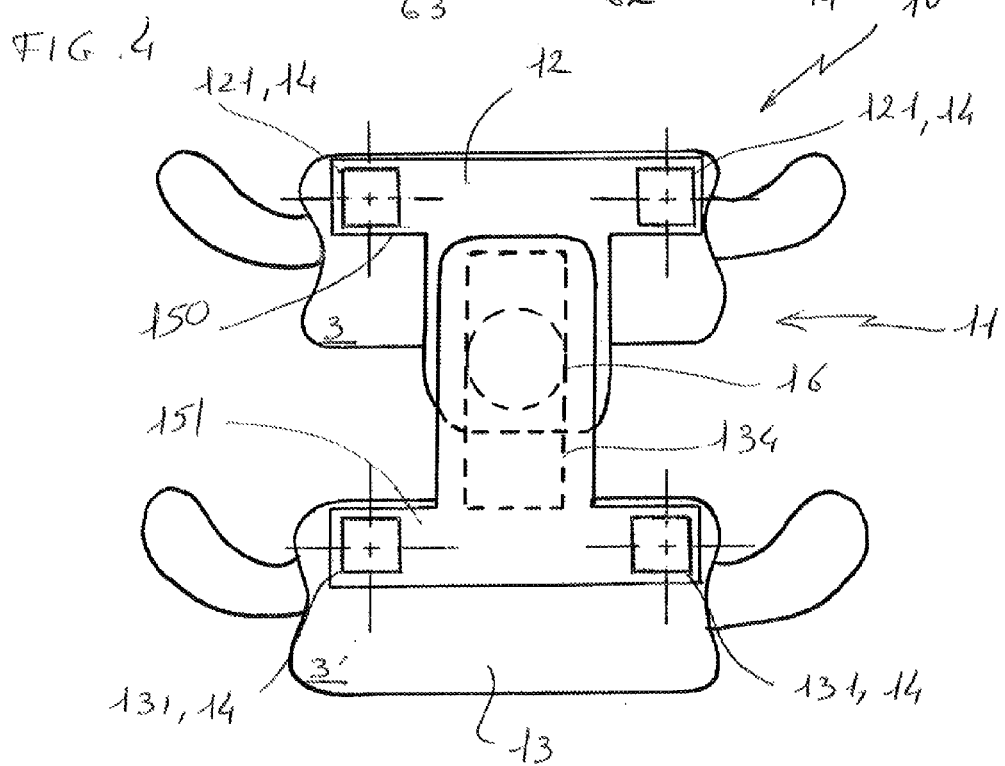

INTERVERTEBRAL DISC PROSTHESIS AND INTERVERTEBRAL PROSTHETIC UNIT

TECHNICAL FIELD

The present invention relates to a self-adjusting and self-stabilizing intervertebral disc intended to replace fibro-cartilage discs providing a connection between the vertebrae of the vertebral column, in particular at the lumbar spine, as well as an intervertebral prosthesis including an intervertebral disc prosthesis associated with a posterior articular prosthesis (posterior interapophyseal articular prosthesis).

PRIOR ART

In the field of surgery of the lumbar portion of the vertebral column, in consideration of the risks inherent to the anterior surgical approach and the difficulty of revision surgery, most surgeons prefer the posterior approach to the lumbar spine.

Thus, the use of a single prosthesis is known. However, the implantation of a prosthesis of this type by the posterior approach requires passing by nerve endings, and therefore poses a high risk for the patient. In addition, the production of such a prosthesis is technically difficult and results in unsatisfactory kinematics of the vertebral column.

To correct these various disadvantages, the use of a bifurcated prosthesis comprising two subassemblies placed on each side of the vertebral column is known. The American patent US 2007/270958 provides an example of such bifurcated prostheses. However, the known bifurcated prostheses can produce adverse effects in patients with said prostheses: they indeed pose a risk of abnormal kinematics, in particular in frontal translation, or dislocation. They therefore are not entirely satisfactory because they do not enable the natural kinematics of the vertebral column to be reproduced. In addition, most of these bifurcated prostheses, for reasons of stability, excessive wear and control of relative movements of the different parts constituting these prostheses, require a posterior articular prosthesis to be put into place, which has the effect of considerably increasing the volume of the assembly thus produced.

In this regard, the present invention is intended to overcome certain disadvantages of the prior art by proposing a new type of bifurcated intervertebral lumbar disc prosthesis that is stable and compact, and with a simple design, enabling the relative movements of its different parts to be controlled, and, thus recreating the natural movements of the vertebral column after said prosthesis has been put into place.

The following terms are used in the present application:
- median plane: the plane that separates the left half from the right half of the body and therefore the plane of the vertebral column,
- median plane of an element: the plane that separates the left half from the right half of this element (the median plane of an element can be a sagittal plane),
- sagittal plane: any plane parallel to the median plane (the median plane of an element can be a sagittal plane),
- frontal plane: the plane that separates the rear half from the front half of the body, and therefore the plane of the vertebral column,
- transverse plane: a plane perpendicular to the median and frontal planes and that separates the body into a top portion and a bottom portion.

SUMMARY OF THE INVENTION

The present invention relates to an intervertebral disc prosthesis, intended to be arranged between an upper vertebra and a lower vertebra, said prosthesis comprising at least one upper plate and at least one lower plate each equipped with anchoring means and intended to be anchored by way of said anchoring means, respectively, in said upper vertebra and lower vertebra, so as to define at least one first lower face of said upper plate provided with a first convex surface opposite at least one first upper face of said lower plate provided with a first concave surface, and comprising at least one second convex surface opposite a second concave surface, said first and second convex surfaces and first and second concave surfaces being separated, in the frontal and sagittal planes, in the assembled configuration, respectively, by a first and second mobile core of which the lower and upper faces are complementary, respectively, to said first and second concave and convex surfaces. This prosthesis is remarkable in that the first and second concave surfaces and the lower faces have a first radius of curvature in the frontal plane and a second radius of curvature in the sagittal plane that are distinct.

Preferably, in the frontal plane, the first and second concave surfaces and the lower faces are tilted with respect to the median plane, respectively, of the first and second mobile cores and lower plates, so that, in the assembled configuration, the centre C2 of the radius of curvature of the first and second concave surfaces and lower faces belongs to the median plane of the prosthesis.

The disc prosthesis with two cores still has a simple design, while being compact and providing good stability. This prosthesis also makes it possible to control relative movements between the different elements constituting it, and thus makes it possible to allow natural movements of the vertebral column.

According to a first embodiment, the prosthesis advantageously comprises two distinct subassemblies, each comprising, respectively, a first and second upper plate, a first and second lower plate and a first and second mobile core, the subassemblies being arranged so as to be capable of being arranged on each side of and symmetrically with respect to the median plane of said prosthesis in said assembled configuration. This configuration must facilitate the positioning of the prosthesis in two phases, a first phase in which a first subassembly is put into place, and a second phase in which a second subassembly is put into place.

According to a second embodiment, especially preferred for the simplicity of implantation, the prosthesis advantageously comprises a single upper plate provided with first and second convex surfaces, a single lower plate provided with first and second concave surfaces, the upper and lower plates being separated in the frontal and median planes by the first and second mobile cores, the first and second convex surfaces and the first and second concave surfaces being arranged so that the first and second mobile cores are arranged on each side of and symmetrically with respect to the median plane of said prosthesis in said assembled configuration. This configuration makes it possible to reinforce the robustness of the prosthesis.

Advantageously, the first convex surface and the first upper face have a centre C1 of a radius of curvature, the second convex surface and the second upper face have a centre C1' of a radius of curvature, the centres C1, C1' being arranged, at least in said assembled configuration, symmetrically with respect to the median plane of the prosthesis. The natural symmetry of the vertebral column is thus respected so as to enable the natural movements of the vertebral column to return after lumbar surgery.

The invention also relates to an intervertebral prosthetic assembly intended to be provided in the place of an intervertebral fibrocartilage disc of the vertebral column between an upper vertebra and a lower vertebra. This intervertebral prosthesis is remarkable in that it comprises at least one lumbar disc prosthesis, in particular as described above, and a posterior articular prosthesis, the posterior articular prosthesis comprising at least two articular blades each intended to be coupled, respectively, to an upper vertebra and a lower vertebra by way of connection means, the articular blades being arranged adjacently and partially tangentially, the articular blades being equipped with guide means arranged so as to allow mobility of the articular blades one with respect to another according to a curve of which the centre C3 of the radius of curvature is provided on the same side of the posterior articular prosthesis as the implantation of the connection means. The proper positioning of the upper and lower vertebrae can thus be ensured in both latero-lateral and anteroposterior directions.

The guide means are preferably provided in the area of tangency of the articular blades and comprise at least one groove provided in one of the articular blades and oriented toward the other articular blade and having a curved profile in the median plane of the articular blade, the other articular blade being equipped with a guide element oriented toward said groove and capable of sliding in said groove.

The guide element can be a ball housed in a recess provided in the articular blade, the recess having a spherical profile. The ball thus enables pivoting in the frontal plane between the articular blades, allowing a lateral tilt of the vertebral column similar to the natural tilt.

In a preferred embodiment, the connection means comprise, for each articular blade, two connection rods intended to be secured to one of the upper and lower vertebrae, the connection rods being arranged on each side of and symmetrically with respect to the median plane of the articular blade, each articular blade comprising a cuff, arranged beyond the area of tangency of the articular blades and capable of receiving one of the connection rods. This configuration enables robust anchoring of the posterior articular prosthesis, ensuring the efficacy thereof over time.

Each connection rod and each corresponding cuff advantageously has complementary polygonal cross-sections making it possible, once the connection rod has been fitted into the cuff, to prevent the connection rod from pivoting with respect to the articular blade.

BRIEF DESCRIPTION OF THE FIGURES

Other features and advantages will become clear from the following description, provided by way of a non-limiting example, of an embodiment of the present invention, with reference to the appended drawings, wherein:

FIG. 3 is a cross-section view, according to plane AA of FIG. 2, of an intervertebral prosthetic assembly according to the invention and associating the intervertebral disc prosthesis of FIGS. 1 and 2 with a posterior articular prosthesis, the posterior articular prostheses being shown in the assembly phase;

FIG. 4 is a posterior frontal view (frontal plane) of the intervertebral prosthetic assembly of FIG. 3 shown on a scale smaller than that of FIG. 3 and entirely assembled.

DETAILED DESCRIPTION OF THE INVENTION

Figure 1:
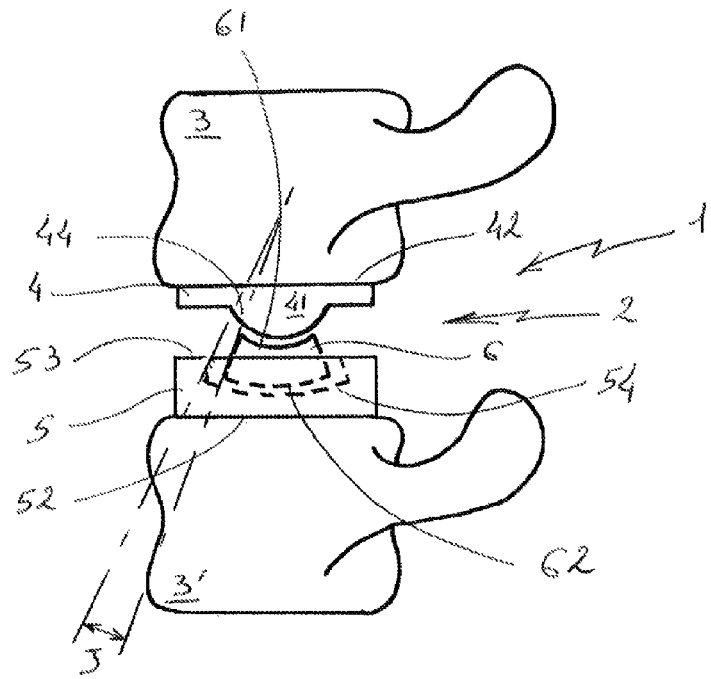
FIG. 1 is a side view (median plane) of an intervertebral disc prosthesis according to the invention, said prosthesis being shown implanted in the vertebral column between upper and lower vertebrae.
Figure 2:
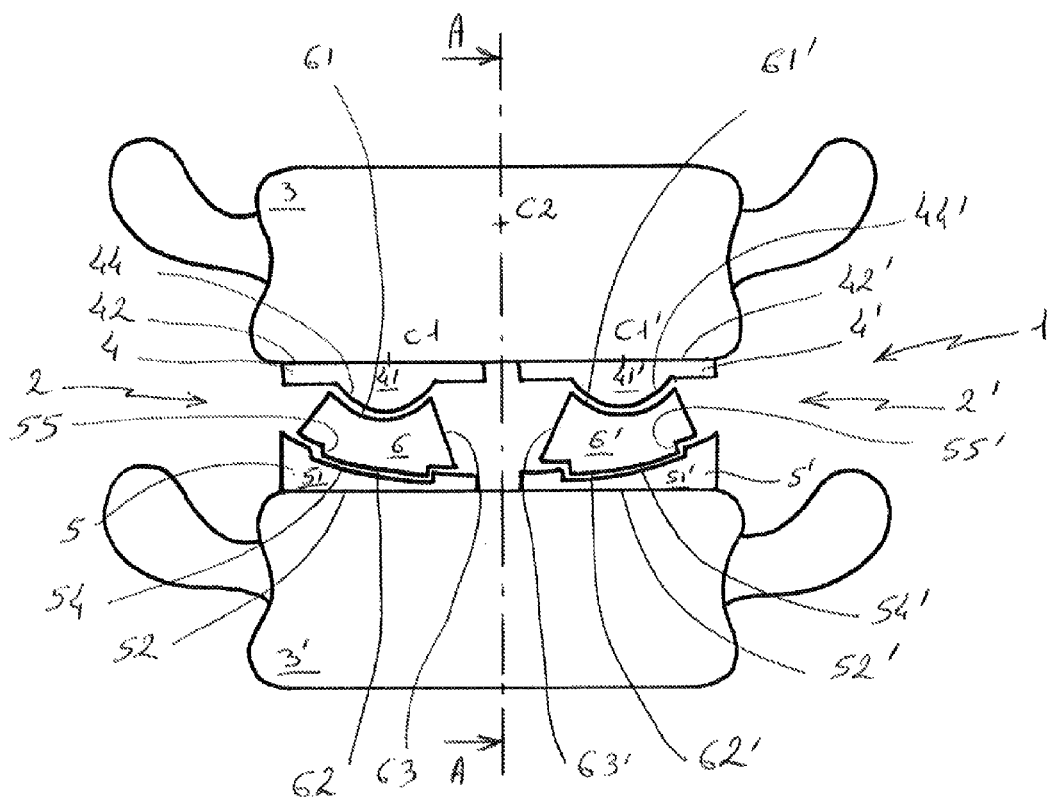
FIG. 2 is a frontal view (frontal plane) of the prosthesis of FIG. 1.
Figure 2A:
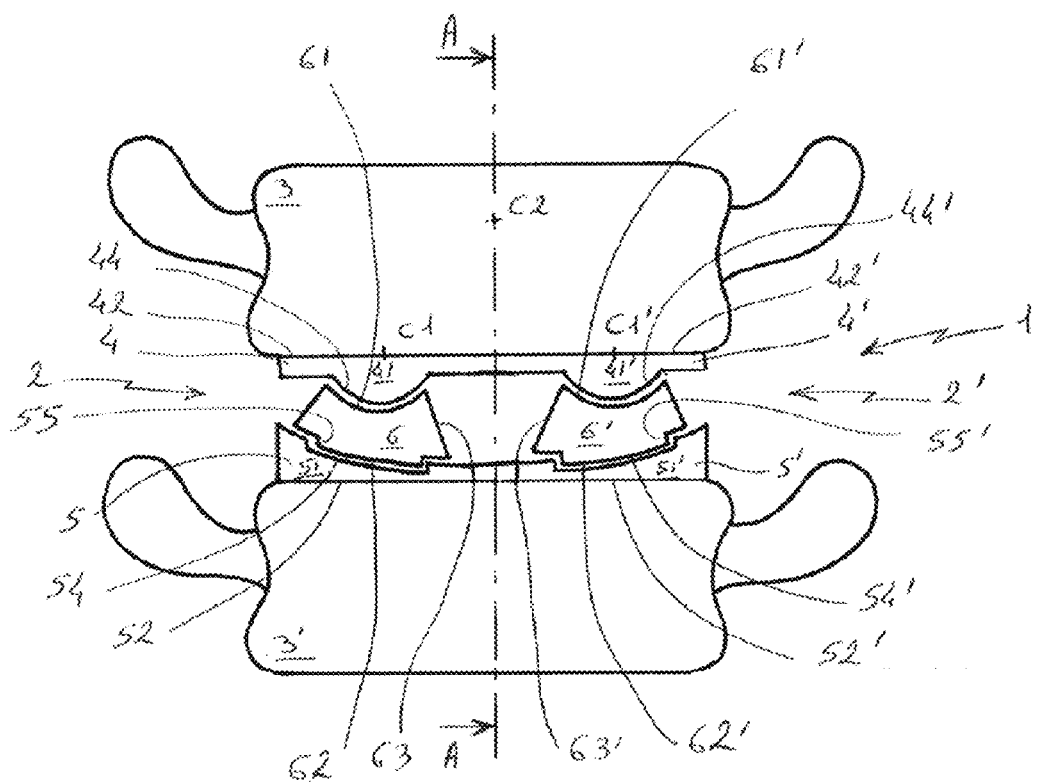
FIG. 2A is a frontal view (frontal plane) of a prosthesis similar to the prosthesis of FIG. 1 and having a single upper plate having the two convex surfaces and a single lower plate having the two concave surfaces.

In reference to FIGS. 1 and 2, the prosthesis 1 according to the invention is intended to be arranged in the place of a fibrocartilage disc ensuring the connection between the vertebrae 3, 3' of the vertebral column, for example the lumbar vertebrae. The prosthesis 1 comprises two subassemblies 2, 2' arranged symmetrically with respect to the median plane of the prosthesis 1 and therefore of the vertebral column. A single subassembly 2 is visible in FIG. 1.

Each subassembly 2, 2' comprises at least three parts, including a first plate called the upper plate 4, 4', a second plate called the lower plate 5, 5' and a mobile core 6, 6' arranged between the two upper and lower plates 4, 5; 4', 5'. The upper plate 4, 4' and the lower plate 5, 5' are thus articulated one with respect to the other by way of the mobile core 6, 6'.

Each upper plate 4, 4' comprises a central body 41, 41' of which the shape and dimensions are complementary to those of the upper vertebra 3 of the spine (located above said upper plate 4). In order to adapt to said upper vertebra 3 and enable the upper plate 4, 4' to be anchored with the bone environment, the upper face 42, 42' of the central body 41, 41' is, on the one hand, slightly dished, and, on the other hand, equipped with anchoring means (not shown). In a preferred embodiment, the anchoring means are teeth projecting perpendicularly from the upper face 42, 42', substantially parallel to one another, perpendicular to the sagittal plane of the prosthesis 1 and of which the cross-section has a general regular trapezoid shape. Each upper plate 4, 4' also comprises a lower face 43, 43' of which the periphery is substantially planar and parallel to the contour of the upper face 42, 42' and of which the central portion is provided with a convex surface 44, 44'. The latter is advantageously in the form of a spherical cap.

In an alternative embodiment not shown, the periphery of the lower face of the upper plate is tilted with respect to the contour of the upper face of the upper plate according to the median plane of the vertebral column in order to adapt to the specific morphology of a patient receiving the prosthesis according to the invention and depending on the stage of replacement of the vertebrae concerned.

Similarly to the upper plates 4, 4', each lower plate 5, 5' includes a central body 51, 51' of which the shape and dimensions are complementary to those of the lower vertebra 3' of the spine (located below the lower plate 5, 5'). In order to adapt to the lower vertebra 3' and enable the lower plate 5, 5' to be anchored with the bone environment, the lower face 52, 52' of the central body 51, 51' is, on the one hand, generally planar and, on the other hand, equipped with anchoring means (not shown). In a preferred embodiment, the anchoring means are teeth similar to those of the upper plates 4, 4' and described above.

To improve the contact and the anchoring of the anchoring means with the upper and lower vertebrae 3, 3', it is possible, for example, to provide a hydroxyapatite-type interface.

The central body 51, 51' of each lower plate 5, 5' also comprises an upper face 53, 53' provided, at its centre, with a dished concave surface 54, 54', advantageously in the form of a spherical cap. In the frontal plane (FIG. 2), the concave surfaces 54, 54' and the upper faces 53, 53' of each lower plate 5, 5' follow a curve of which the centre C2 (visible in FIG. 2) is located in the median plane of the prosthesis 1 and therefore of the vertebral column. Thus, the concave surfaces 54, 54' and the upper faces 53, 53' are generally tilted with respect to the median plane of the prosthesis 1 and one with respect to the other. This tilt, in particular of the upper faces 53, 53', is such that the outer edges of the lower plates 5, 5' are higher than the inner edges of the same lower plates 5, 5'.

Each concave surface 54, 54' is extended by edges 55, 55', substantially perpendicular to the curve of the corresponding concave surface 54, 54', these edges 55, 55' joining the corresponding upper face 53, 53'. As described in detail below, these edges 55, 55' define a peripheral stop making it possible to limit the movements of each of the mobile cores 6, 6' with respect to the corresponding lower plate 5, 5' and therefore the movements of the prosthesis 1 in at least the two latero-lateral and anteroposterior directions with respect to the positioning of each subassembly 2, 2' in the vertebral column. In addition, the centre C2 of the radius of curvature of the upper faces 53, 53' advantageously coincides with that of the concave surfaces 54, 54'.

Each mobile core 6, 6' comprises an upper face 61, 61', a lower face 62, 62' and a peripheral face 63, 63' that connects the upper and lower faces 61, 62; 61', 62' to one another.

Each upper face 61, 61' of the mobile cores 6, 6' has a concavity, advantageously in the form of a spherical cap, congruent with the convex surface 44, 44' of the upper plate 4, 4'. In a preferred embodiment, the entirety of the latter is covered by the concavity of the upper face 61, 61'. In another preferred embodiment that may or may not be combined with the previous embodiment, the centre C1, C1' of the radius of curvature of each upper face 61, 61' (visible in FIG. 2) advantageously coincides with that of the corresponding convex surface 44, 44'.

Each lower face 62, 62' of the mobile cores 6, 6' comprises a central portion advantageously in the form of a concave spherical cap. This central portion is provided, substantially at its middle, with an appendage in the form of a lug of which the edges are substantially perpendicular to the lower face 62, 62' so as to cooperate with the edges 55, 55' in order to form the peripheral stop limiting the movements in the two latero-lateral and anteroposterior directions of the prosthesis 1. Consequently, each lower face 62, 62' defines an annular surface around the lug. In a preferred embodiment, the peripheral face 63, 63' is generally frustoconical. Each lower face 62, 62' of the mobile cores 6, 6' is concave and such that the centre C2 of its radius of curvature (shown in FIG. 2) advantageously coincides with that of the concave surface 54, 54'. Each of the annular and lower faces 62, 62' of the mobile cores 6, 6' is congruent, respectively, with the concave surface 54, 54' and the upper face 53, 53'.

In addition, it is clearly understood that, to put each of the mobile cores 6, 6' into place, it is necessary for the lug to have dimensions smaller than those of the central portion in the form of a concave spherical cap.

In an alternative embodiment not shown, the prosthesis comprises a single upper plate provided with first and second convex surfaces, a single lower plate provided with first and second concave surfaces, the upper and lower plates being separated in the frontal and median planes by the first and second mobile cores. In this alternative embodiment, the first and second convex surfaces and the first and second concave surfaces are provided so that the first and second mobile cores are arranged on each side of and symmetrically with respect to the median plane of the prosthesis in the assembled configuration.

In these two cases, a centre-to-centre spacing will be provided between the mobile cores 6, 6' and between the centres C1 and C1'.

To obtain an effective articulation between each upper plate 4, 4' and each corresponding lower plate 5, 5' around the mobile cores 6, 6', it is understood that the upper plates 4, 4' and lower plates 5, 5' and the mobile cores 6, 6' must be such that the upper faces 61, 61' of the mobile cores 6, 6' are in contact with the corresponding convex surfaces 44, 44' of the upper plates 4, 4' and that the lower faces 62, 62' of the mobile cores 6, 6' are in contact with the concave surfaces 54, 54' of the lower plates 5, 5'. Such a configuration makes it possible to allow a relative movement in the form of a tilt between the upper and lower plates 4, 5; 4', 5' by way of the mobile cores 6, 6'.

In reference to the example shown, and preferably, the centres C1, C1' of the radii of curvature of the upper faces 61, 61' and the convex surfaces 44, 44' and the centre C2 of the radii of curvature of the lower faces 62, 62' and the concave surfaces 54, 54' are provided on the same side of the subassemblies 2, 2' of the prosthesis 1, namely that of the upper plates 4, 4'.

In addition, the centre C2 is transversally offset with respect to the centres C1, C1' so that the radius of curvature of the lower faces 62, 62' and of the concave surfaces 54, 54' is greater than that of the upper faces 61, 61' and of the concave surfaces 54, 54'. The distance separating the centres C1, C1' and C2 is dependent upon the intervertebral space and is advantageously as small as possible.

In order to optimize the articulation and in particular the gliding between the different elements, the radius of curvature of the lower faces 62, 62' is smaller than that of the concave surfaces 54, 54' and the radius of curvature of the upper faces 61, 61' is greater than that of the concave surfaces 54, 54'.

A person skilled in the art will have no problem sizing said radii of curvature, and consequently obtaining relative rates of movement of the different elements constituting the prosthesis 1, enabling said prosthesis 1 to be self-adjusting and self-stabilizing. In addition, it is clearly understood that said radii of curvature can be adjusted according to the position of the prosthesis 1 along the lumbar spine of the vertebral column, because the rates of relative movement are also dependent upon said position.

Finally, in reference to FIG. 1, an angular clearance J is preserved in the sagittal plane, on each side of the mobile cores 6, 6' between each of the mobile cores 6, 6' and the corresponding lower plate 5, 5' in order to allow a relative movement of the mobile cores 6, 6' and the lower plates 5, 5'. This design of the prosthesis 1 enables the self-centring of the mobile cores 6, 6' and the self-adjustment of the prosthesis 1 in order to respect the natural physiological kinematics of the lumbar spine. Indeed, it is then understood that the mobile cores 6, 6' will, by moving, compensate for the movements of the upper plates 4, 4' with respect to the lower plates 5 in the four directions. The prosthesis 1, according to the invention, thus enables control and limitation of the forces exerted on the posterior articulations, thereby preventing problems of hyperpressure and resulting arthrosis.

The upper and lower plates 3, 3', 4, 4' and the mobile cores 6, 6' are advantageously produced using non-metallic materials enabling MRI's to be performed in particular so as to enable the spinal cord to be examined. Thus, for example, the upper plates 4, 4' and lower plates 5, 5' are made of polyether ether ketone and the mobile cores 6, 6' are made of ceramic. These two materials also have the advantage of having a low mutual friction coefficient enabling easy gliding of the parts, one against the other, and thus good articulation of the upper plates 4, 4' and lower plates 5, 5' with respect to the mobile cores 6, 6'.

A person skilled in the art will have no problem sizing the different elements constituting the prosthesis 1 according to the invention, respecting in particular the minimal thicknesses associated with the nature of the materials used. Thus, for example, for each lower plate 5, 5', we will not go below a thickness of 1.3 mm separating the concave surface 54, 54' and the lower face 52, 52'.

In addition, it is clearly understood that the intervertebral space varies according to the patient's morphology. It is therefore important to have a prosthesis 1 available in different dimensions, in particular different heights. With the prosthesis 1 according to the invention, the total height may be adjusted by modifying only the thickness of the mobile cores 6, 6'. It is therefore possible, while using the standard upper plates 4, 4' and lower plates 5, 5', to vary the height of the prosthesis 1 as needed.

In reference to FIGS. 3 and 4, the present invention also relates to an intervertebral prosthetic lumbar disc assembly 10 including a lumbar disc prosthesis 1, in particular and preferably, but not necessarily, as described above, associated with a posterior prosthesis 11. In this example, the posterior articular prosthesis 11 comprises a first and a second articular blade 12, 13 coupled by way of connection means 14 described below, respectively, to the upper and lower vertebrae 3, 3' of the intervertebral space where the prosthesis 1 is put into place. The first and second articular blades 12, 13 are arranged adjacently and partially tangentially with respect to one another so as to partially overlap and define at least one area of tangency. The articular blades 12, 13 have a complementary curved profile so that the space between the first and second articular blades 12, 13 is substantially constant along their profile. The two articular blades 12, 13 are thus arranged congruently and not in connection with one another. The curved profile of the first and second articular blades 12 is chosen so that the centre C3 of the radius or radii of curvature is placed on the same side of the posterior articular prosthesis 11 as the connection means 14.

The first and second articular blades 12, 13 are each provided, opposite the area of tangency, with a cross-member 150 151 extending on each side of the first and second articular blades 12, 13. These cross-members 150, 151 make it possible to have a limited width of the posterior articular prosthesis 11 in the area of tangency and thus reduce the bulk and facilitate the mobility thereof while enabling effective anchoring with the vertebra 3, 3'.

Opposite the area of tangency, the first and second articular blade 12, 13 each comprise two cuffs 121, 131 with polygonal, for example square, cross-sections, and arranged on each side of the median plane of each corresponding articular blade 12, 13, at the ends of the cross-members 150, 151. The posterior articular prosthesis 11 thus comprises four cuffs 121, 131. The posterior articular prosthesis 11 also comprises four connection rods 14, with a polygonal, for example square, cross-section, and complementary to that of the cuffs 121, 131. The connection rods 14 can thus be received in the cuffs 121, 131, with the complementary polygonal cross-sections preventing the pivoting of each connection rod 14 with respect to the corresponding articular blade 12, 13. This makes it possible to thus reinforce the robustness and stability of the intervertebral prosthetic assembly.

Each transverse connection rod 14 is secured to the vertebra 3, 3' by way of a pedicle screw (not shown), preferably conical, screwed into the vertebra 3, 3' and coupled to the transverse connection rod 14. Thus, the first articular blade 12, called the upper blade, is connected to the upper vertebra 3 and the second articular blade 13 is connected to the lower vertebra 3'.

The first and second articular blades 12, 13 are equipped, in their area of tangency, with means for guiding by gliding, allowing relative mobility between the first and second articular blades 12, 13 according to a curve.

According to an alternative embodiment, the first articular blade 12 comprises a groove 134 oriented toward the second articular blade 13 and having a curved profile in the median plane of the first articular blade 12. The second articular blade 13 is equipped with a guide element 16 oriented toward the groove 134 and capable of circulating in the groove 134. The guide element is, in this case, a ball 16, half of which is housed in a recess 124 having a spherical profile provided in the second articular blade 13. The groove 134 is therefore capable of receiving the second half of the ball 16 and of allowing its movement along its profile in an arc of circle. Thus, when the first and second articular blades 12, 13 are each respectively attached to the upper and lower vertebrae 3, 3', the first articular blade 12 is placed toward the inside of the intervertebral area and the second articular blade 13 is placed toward the outside of the intervertebral area so that the ball 16 is arranged between the two articular blades 12, 13, housed respectively in the recess 124 and in the groove 134. The two articular blades 12, 13 each also have a median plane of symmetry, the ball 16 and the groove 134 being provided in the median plane of the intervertebral prosthetic assembly 10.

In an alternative embodiment not shown, the groove is provided on the second articular blade and the guide element is provided on the first articular blade. In yet another alternative embodiment not shown, the posterior articular prosthesis comprises a greater number of articular blades and/or each blade comprises, respectively, a plurality of grooves and a plurality of guide elements. The first articular blade can also comprise at least one groove and one guide element cooperating respectively with a guide element and a groove provided on the second articular blade.

The curved profiles of the groove 134 and the first and second articular blades 12, 13 are circular and concentric. The first and second articular blades 12, 13 can thus slide one with respect to the other congruently and not in connection, while being guided according to a curved trajectory, in this example, circular. To enable optimal gliding between the first and second articular blades 12, 13, the radius of curvature of the outer face 122 of the first articular blade 12 is smaller than the radius of curvature of the inner face 133 of the second articular blade 13. The connection and the distance between the first and second articular blades 12, 13 is in this case ensured by the ball 16 and the groove 134. Because of their concentric profile, the first and second articular blades 12, 13 can also pivot about the ball 16.

According to an important feature of the invention, the centre C3 of the curved profiles of the groove 134 and the first and second articular blades 12, 13 is advantageously aligned with the centres C1, C1' (centres, respectively, of the radii of curvature of said first convex surface 44 and first upper face 61 and of the radii of curvature of said second convex surface 44' and second upper face 61').

In the example shown, each transverse connection rod 14 is rectilinear. In an alternative embodiment not shown, each transverse connection rod can be curved.

The recesses of the cuffs 121, 131 are blind. In an alternative embodiment not shown, these recesses can be through-recesses so as to enable the connection rods to extend beyond the rear face of the posterior articular prosthesis. This alternative embodiment is particularly advantageous in particular in the case of a prosthetic intervention concerning two adjacent intervertebral spaces. Indeed, the same connection rod can thus serve as a support for a first articular blade of a first intervertebral space and a second articular blade of a second intervertebral space.

Finally, the groove 134 is blind at its ends. The ends of the groove 134 thus serve as stops so as to limit the movement of the ball 16 in the groove 134 so as to limit the relative movement between the two articular blades 12, 13. In an alternative embodiment not shown, the groove can also be a through-groove, in particular at the end opposite that with the cuff. This configuration with a through-groove enables the assembly of the articular blades with respect to one another to be facilitated.

For example, the first and second articular blades 12, 13 are made of a material identical to that of the conical pedicle screws, namely a chromium/cobalt/molybdenum Cr—Co—Mb alloy, or titanium or ceramic, and coated with polyethylene, as the case may be.

According to an alternative embodiment not shown, the centre of the radius of curvature of the outer face of the first articular blade and the inner face of the second articular blade is located on a line separated from the centre of the radius of curvature of the convex surface of the upper plate of the disc prosthesis by two-thirds of the distance separating the centres of the radii of curvature of the convex surfaces of the upper plates and the centre of the radius of curvature of the concave surfaces of the lower plate.

According to another embodiment not shown, the first and second articular blades have a curved profile and have a V-shaped transverse cross-section, one in relief and the other recessed, so as to be capable of fitting together, the V-shaped cross-sections defining the guide means. This embodiment has the advantage of leaving more lateral room for the muscle bundle surrounding the vertebral column.

According to yet another alternative embodiment not shown, the articular blades can each have, in the median plane, a hyperbolic paraboloid portion replacing the circular portions. These hyperbolic paraboloid portions are congruent and tangential so that one portion slides along the other portion. The hyperbolic paraboloid portions can comprise a V-shaped transverse cross-section or a groove cooperating with a guide element.

INDUSTRIAL APPLICATION

The invention makes it possible to produce, in particular, intervertebral disc prostheses as well as intervertebral prosthetic assemblies capable of being implanted in the lumbar area of the vertebral column.

It goes without saying that the present invention is not limited to the preferred embodiment example or to the implementation described, and that the prosthesis and the intervertebral prosthetic assembly can be modified or adapted according to needs, anatomical specificities, or particular requirements, without going beyond the scope of the invention.

The invention claimed is:

1. An intervertebral prosthetic assembly intended to be provided in the place of an intervertebral fibrocartilage disc of the vertebral column between an upper vertebra and a lower vertebra, comprising at least one intervertebral disc prosthesis and a posterior articular prosthesis, the intervertebral disc prosthesis being intended to be arranged between the upper vertebra and the lower vertebra, the intervertebral disc prosthesis comprising:
   at least one upper plate and at least one lower plate each equipped with anchoring means and intended to be anchored by way of said anchoring means, respectively, in said upper and lower vertebrae, so as to define at least one first lower face of said at least one upper plate provided with a first convex surface opposite at least one first upper face of said at least one lower plate provided with a first concave surface, and comprising at least one second convex surface opposite a second concave surface;
   said first and second convex surfaces and first and second concave surfaces being separated, in the frontal and sagittal planes, in an assembled configuration, respectively, by first and second mobile cores each having a lower face and an upper face, the lower and upper faces of the first and second mobile cores being complementary, respectively, to said first and second concave and convex surfaces,
   wherein said first and second concave surfaces and said lower faces of the first and second mobile cores have a first radius of curvature in the frontal plane and a second radius of curvature in the sagittal plane that are distinct; and
   wherein said first convex surface and said upper face of the first mobile core have a center C1 of a radius of curvature, and said second convex surface and said upper face of the second mobile core have a center C1' of a radius of curvature, said centers C1, C1' aligned on a line;
   the posterior articular prosthesis comprising:
   at least two articular blades each intended to be coupled to a respective one of the upper and the lower vertebrae by way of connection means, said articular blades being arranged adjacently and partially tangentially, such that a convex portion of a first articular blade is arranged adjacently to a concave portion of a second articular blade, said articular blades being equipped with guide means arranged so as to allow mobility of said articular blades one with respect to another according to a curve having a radius of curvature,
   wherein said guide means are arranged so that said curve of relative mobility of said articular blades is an arc of a circle having a center C3 which is provided on the same side of said posterior articular prosthesis as the coupling of said connection means to the respective vertebrae,
   wherein C3 is disposed on the line on which the centers C1 and C1' are aligned, and
   wherein, along the line, the center C3 is separated from each of the centers C1 and C1' by two-thirds of a distance separating each of the centers C1 and C1' from a center C2 of the first radius of curvature of said first and second concave surfaces and said lower faces of the first and second mobile cores.

2. The intervertebral prosthetic assembly according to claim 1, wherein, in the frontal plane, said first and second concave surfaces and said lower faces of the first and second mobile cores are tilted with respect to the median plane, respectively, of said first and second mobile cores and the at least one lower plate, so that, in the assembled configuration, the centre center C2 of the first radius of curvature of said first and second concave surfaces and said lower faces of the first and second mobile cores lies in the median plane of said prosthesis.

3. The intervertebral prosthetic assembly according to claim 2, wherein said centers C1, C1' are arranged, at least in said assembled configuration, symmetrically with respect to the median plane of said prosthesis.

4. The intervertebral prosthetic assembly according to claim 3, wherein, in the frontal plane, the center C2 of the first radius of curvature of said first and second concave surfaces and said lower faces of the first and second mobile cores is transversally offset with respect to said centers C1, C1'.

5. The intervertebral prosthetic assembly according to claim 1, comprising a single upper plate provided with said first and second convex surfaces, a single lower plate provided with said first and second concave surfaces, said upper and lower plates being separated in the frontal and sagittal planes by said first and second mobile cores, said first and second convex surfaces and said first and second concave surfaces being arranged so that said first and second mobile cores are arranged on each side of and symmetrically with respect to the median plane of said prosthesis in said assembled configuration.

6. The intervertebral prosthetic assembly according to claim 1, wherein said guide means are provided in an area of the tangency of said articular blades and comprise at least one groove provided in one of said articular blades and oriented toward the other articular blade and having a curved profile in the median plane of said articular blade, the other articular blade being equipped with a guide element oriented toward said groove and toward a portion of said one articular blade defining a bottom of the groove, the guide element being capable of sliding in said groove along its bottom.

7. The intervertebral prosthetic assembly according to claim 6, wherein said guide element is a ball housed and movable in a recess provided in said other articular blade, said recess having a spherical profile.

8. The intervertebral prosthetic assembly according to claim 1, wherein said connection means comprise, for each articular blade, two connection rods to be secured to the respective one of said upper and lower vertebrae, each of said two connection rods being arranged on either side of and symmetrically with respect to the median plane of said articular blade, each articular blade comprising a cuff, arranged beyond an area of the tangency of said articular blades and capable of receiving one of said connection rods.

9. The intervertebral prosthetic assembly according to claim 8, wherein each connection rod and each corresponding cuff have complementary polygonal cross-sections, thereby preventing, once said connection rod has been fitted into said cuff, said connection rod from pivoting with respect to said articular blade.

10. The intervertebral prosthetic assembly according to claim 8, wherein each connection rod is coupled to a pedicle screw capable of being screwed into the respective one of said upper and lower vertebrae.

\* \* \* \* \*